(12) United States Patent
Gonon (10) Patent No.: US 6,423,027 B1
(45) Date of Patent: Jul. 23, 2002

(54) APPARATUS AND METHOD FOR DISSECTION BY PRESSURIZED LIQUID AND INJECTION BY PRESSURIZED PROJECTION OF A TREATING PRODUCT

(75) Inventor: Bertrand Gonon, Lyons (FR)

(73) Assignee: Saphir Medical Products GmbH, Schwaig (DE)

( * ) Notice: Subject to any disclaimer, the term of this patent is extended or adjusted under 35 U.S.C. 154(b) by 0 days.

(21) Appl. No.: 09/532,904

(22) Filed: Mar. 22, 2000

(30) Foreign Application Priority Data

Mar. 22, 1999 (DE) .......................... 199 12 844

(51) Int. Cl.[7] .............................. A61M 1/00
(52) U.S. Cl. ........................... 604/27; 604/21
(58) Field of Search .............. 604/27, 22, 30, 604/35, 31, 32, 33, 36, 43, 119, 150, 152, 39, 40, 42, 118

(56) References Cited

U.S. PATENT DOCUMENTS

| | | | |
|---|---|---|---|
| 4,205,677 A | 6/1980 | Engstrom | |
| 4,519,385 A | 5/1985 | Atkinson et al. | |
| 4,655,197 A | 4/1987 | Atkinson | |
| 4,676,779 A | 6/1987 | Mayoral | |
| 4,702,733 A | 10/1987 | Wright et al. | |
| 4,759,349 A | 7/1988 | Betz et al. | |
| 5,322,506 A | 6/1994 | Kullas | |
| 5,425,703 A * | 6/1995 | Feiring | 604/103.01 |
| 5,605,537 A | 2/1997 | Ivey | |
| 5,674,226 A | 10/1997 | Doherty et al. | |
| 5,735,815 A | 4/1998 | Bair | |
| 5,810,763 A * | 9/1998 | Feiring | 604/21 |
| 6,106,494 A * | 8/2000 | Saravia et al. | 604/151 |
| 6,179,816 B1 * | 1/2001 | Mottola et al. | 604/264 |
| 6,322,533 B1 * | 11/2001 | Gonon | 604/35 |

FOREIGN PATENT DOCUMENTS

| | | |
|---|---|---|
| DE | 30 19 115 A1 | 12/1981 |
| DE | 37 15 418 A | 11/1987 |
| EP | 0 346 712 A2 | 12/1989 |
| EP | 0 470 781 A1 | 2/1992 |
| EP | 0 489 496 A1 | 6/1992 |
| EP | 0 551 920 A1 | 7/1993 |
| EP | 0 636 345 A1 | 2/1995 |
| EP | 0 879 578 A1 | 11/1998 |
| EP | 0 888 750 A1 | 1/1999 |
| FR | 1 378 042 | 2/1965 |
| FR | 2 706 276 | 12/1994 |
| WO | WO 94/10917 | 5/1994 |
| WO | WO 94 28807 | 12/1994 |
| WO | WO 96/01079 | 1/1996 |
| WO | WO 96/35469 | 11/1996 |
| WO | WO 96/39952 | 12/1996 |
| WO | 97/03713 | 2/1997 |
| WO | WO 97/49441 | 12/1997 |
| WO | WO 98/55033 | 12/1998 |
| WO | WO 99/33510 | 7/1999 |

* cited by examiner

Primary Examiner—Teresa Walberg
Assistant Examiner—Vinod D. Patel
(74) Attorney, Agent, or Firm—Armstrong, Westerman & Hattori, LLP (57) ABSTRACT

The pressurized liquid dissection apparatus has means for pressurization of working liquids and treatment liquids, controlled discharge means for a pressurized jet, and means for switching or mixing a treatment product with the working liquid or multiplexing means during pulsed mode operation of pressurized pulsed jets. The procedure consists in pressurized spraying of at least one treatment product with the pressurized surgical working jet or separately therefrom but with the same apparatus and during the same intervention so as to realize a surgical act and a therapeutic act during one and the same intervention. This invention is applicable in the surgical and medical fields.

19 Claims, 7 Drawing Sheets

APPARATUS AND METHOD FOR DISSECTION BY PRESSURIZED LIQUID AND INJECTION BY PRESSURIZED PROJECTION OF A TREATING PRODUCT

The present invention concerns a pressurized liquid dissection apparatus enabling simultaneous pressurized spraying of a treatment product, as well as the procedure implemented in such an apparatus.

The use of a pressurized liquid jet is known in the medical and surgical field and enables to advantageously realize all types of incisions, dissections, ablations, or disaggregations. Numerous pressurized liquid pulsed or continuous jet apparatuses, with or without aspiration, have been described within the framework of patent applications. Examples which may be cited in this regard include the applications WO 97/03713, FR 2,780,268 and FR 2,779,734 in the name of SAPHIR MEDICAL or the application EP 0,636,345 in the name of SENTINEL MEDICAL.

Pressurized liquid jet surgical apparatuses advantageously enable replacement, for certain delicate medical or surgical interventions, of the conventional mechanical cutting tools such as scalpels, which are not very precise and are particularly traumatizing, or lasers, which make a particularly fine, precise, incision, but by means of burning tissues, resulting in necrosis of adjacent tissues, both undesirable and difficult to heal, as well as ultrasonic bistouries offering reduced efficacy and necessitating frequent and precise adjustments.

In contrast, pressurized liquid jet apparatuses enable the realization of a clean, precise, incision without damaging tissues adjacent to the target. Moreover, their cost is moderate, in any event clearly less, for example, than that of laser or ultrasonic apparatuses, and they are particularly flexible to use. In fact, many operational parameters, such as the pressure of the working liquid, the force or frequency of aspiration, and the pulse duration, if a pulsed jet is used, may be modified in order to optimize the effect obtained. Depending on the value of these parameters, it is possible to obtain a more or less incisive tissue cutting action and a more or less extensive dissection effect, resulting, for example, in incision of the softest tissues and leaving the other tissues intact.

Pressurized liquid jet surgical apparatuses are thus particularly appropriate to realize, for example, the ablation of soft tissues, because they are capable of emulsifying these tissues without damaging the adjacent tissues. The emulsified tissues are then easily removed from the operative site by aspiration.

In order to increase the benefits of the surgical intervention for the patient, it would often be desirable to be able to inoculate the patient with a treatment product at the time of the operation. This product may have any therapeutic activity associated with the patient's pathology or with the course of the surgery. It could be, for example, a preparatory agent for the surgery, useful in its course, increasing its beneficial effects, limiting the risks of postoperative complications, or combating secondary effects associated with surgical trauma. It could also be any therapeutic agent useful in the treatment of the problem or of the disease of the patient in question.

However, with the surgical instruments known in the prior art, the direct and simultaneous application of a treatment product is not possible. The application of a treatment product usually occurs before or after the operation and/or by means of an injection not made at the site of the operation, which is most often inaccessible. The therapeutic agent must, consequently, circulate within the blood system of the patient until it reaches its target. This circulation may cause a reduction in the efficacy of the treatment product and provoke undesirable secondary effects by also affecting tissues other than those targeted.

If carried out during the operation, the application must be effected with an instrument other than the dissection instrument, a situation which implies a loss of time and concentration for the surgeon, who must change instruments during the course of the operation. This is all the more complicated when the intervention is non-invasive, i.e., is performed percutaneously by means of instruments carried by or integrated into a catheter advanced to the site of the intervention.

The object of the invention is to enable application of a treatment product directly at the site of the surgical or medical intervention simultaneously with its realization and to do so with the same apparatus.

To solve this technical problem, the pressurized liquid dissection apparatus according to the invention includes means of switching or mixing a treatment product with the working liquid or multiplexing means in the case of a pulsated system of pressurized pulsed jets.

Thus, the surgeon may, using the apparatus according to the invention, make the incision directly with the treatment product using it as the working liquid. Since the therapeutic agent is usually rather expensive, it is also possible to use a mixture of conventional working liquid, preferably physiological serum, and treatment product.

Starting from this basic principle, it is possible to conceive of numerous other variants of the apparatus according to the invention. This may, for example, include a control means enabling the person performing the operation to trigger, to stop, and/or to modify the parameters of the pressurized working liquid jet and that of the treatment product, based on his needs, with the two liquids possibly leaving the apparatus through two different orifices or through a single discharge orifice connected by a switching or mixing element with two separate or with one mixed pressurized supply.

A preferred embodiment of the apparatus according to the invention provides a pulsed pressurized liquid jet. It may then have a multiplexer enabling combining the pulses of the working liquid and the treatment product within the discontinuous pulse train constituting the pulsed jet. The parameters of the various pulses, their nature, and their succession may be modified and programmed depending on the needs of the surgeon, of the patient, and of the type of surgery performed, in order to optimize the result of the intervention.

The apparatus and the procedure according to the invention afford very significant advantages compared to the known systems. Thanks to them, the treatment liquid may be sprayed directly under pressure onto the operative site itself. The product thus arrives directly at its site of action with maximum efficacy. The risks of the application affecting organs or tissues not involved are greatly reduced.

The application of the treatment product occurs at the time of the incision and simultaneously during the course of the intervention, at the most appropriate time to ensure maximum efficacy of the treatment product. The force of the pressure of the liquid jet also enables better penetration and diffusion of the treatment product deep into the tissues where it diffuses rapidly and extensively, a situation which further reinforces its efficacy.

Moreover, the application of the therapeutic agent is simple and rapid and takes place without changing the apparatus and without interfering with the concentration of the surgeon.

The medical or surgical intervention procedure according to the invention enables realization of a surgical and therapeutic act on the body of a living being, in a single intervention, and with a single surgical or medical apparatus of which the working fluid is a pressurized biocompatible liquid. To accomplish this, during the intervention, and with this same apparatus, a treatment product, mixed or not with the working liquid, is sprayed under pressure, thus improving its penetration and diffusion into the tissues. The treatment product preferably is in liquid form.

In a variant, it is possible to also spray a therapeutic agent before surgery in preparation therefor or an agent to complete the surgical task after the surgery.

The apparatus and procedure according to the invention may be suitable for a large variety of medical or surgical interventions on all the organs of the body of a living being, of which only a few examples will be described in the following and in the body of the description.

The surgical apparatus for the invention is, for example, particularly suited to performing interventions of the type of transmyocardial revascularization, because it enables application of angiogenic substances simultaneously with the creation of revascularization channels within the ischemic region of the myocardium.

Another example of application of the apparatus according to the invention and of the procedure implemented thereby is the treatment of vascular disorders such as thromboses.

Moreover, because of the adjustable intensity of its dissection effect, this apparatus is also particularly advantageous for interventions on soft tissues such as those, for example, of the liver. It can be used advantageously to realize grafts, with the apparatus according to the invention enabling simultaneous application of anti-rejection substances, or removal of cancerous tumors from this organ.

Other characteristics and advantages of the invention will be disclosed in the following description, provided by way of example and accompanied by drawings, wherein.

The pressurized liquid dissection apparatus according to the present invention will now be described in detail with reference to FIG. 1 through 7. Equivalent elements depicted in the various figures bear the same numerical references. The portions of circuits in which the working liquid circulates are depicted by heavy gray lines. The portions of circuits designed for the treatment product are depicted by heavy black lines. The continuous heavy lines represent a continuous liquid jet; the broken heavy lines, a pulsed jet.

The surgical apparatus according to the present invention was depicted schematically in FIG. 1 through 7. It is an apparatus 1 capable of delivering one or a plurality of pressurized jets of sterile liquid, for example, against a tissue to be cut or a substance to be disaggregated.

This apparatus includes a pressurized liquid generator 2 connected to a supply 3 of working liquid. This supply may be, for example, a plastic pouch containing the working liquid enclosed in a housing which may be filled with a neutral gas in order to compress the pouch and to pressurize the liquid. The pressure of the liquid jet generated may be adjustable in order to adapt it as needed. The pressure inside the housing is variable, preferably between 0.3 and 200 bar, more preferably between 0.3 and 100 bar, depending on the application. The housing is also heated thermostatically to a temperature near or slightly higher than 37° C. such that the working liquid reaching the operative site is approximately the same temperature as that of the body of the patient.

A typical pressure value for pure dissection applications is approximately 30 bar.

The working liquid used is preferably physiological serum used at a pressure adapted to the application. Consequently, the incision is completely sterile and nonaggressive to tissues. Thus, the problems of sterilization of conventional needles and surgical apparatuses are limited and the risks of complications are reduced.

Obviously, other liquids may be used as sterile working fluids, such as a saline, glucose, Ringer's lactate, or hydroxyethyl starch solution or a mixture thereof.

The sterile working liquid is fed to a hand unit 4 enabling the surgeon performing the intervention to control the triggering of the working liquid jet and to guide it. The hand unit 4 has an ergonomic body 5, enabling easy holding and handling and capable of presenting control elements, such as a pushbutton 6, as well as an active end 7, for example, a tube 8 which delivers the pressurized liquid jet. The end tube 8, cylindrical in shape, for example, includes a conduit 9 inside which the working liquid passes to an end orifice 10 through which the liquid jet under pressure 11 shoots in order to realize a surgical task of cutting, dissection, or disaggregation.

The surgical apparatus 1 preferably includes an aspiration system 12 connected to a vacuum source 13, for example, the general vacuum circuit of the hospital. In the various embodiments depicted in FIG. 1 through 7, the aspiration system ends in an aspiration conduit 14, for example, generally cylindrical in shape, located at the end 7 and concentric to the conduit 9. The aspiration conduit 14, opening in proximity to the operative zone enables aspiration of the working liquid and the small debris during the course of the dissection task, thus improving the efficacy of the incision and the visibility of the operative zone for the surgeon.

For better efficacy, the surgical apparatus according to the present invention is preferably a pulsed jet apparatus delivering the pressurized liquid by a blast in the form of a discontinuous pulse train constituting elementary pressurized liquid jets. A blast may also be made up of a single pulse. In this embodiment depicted in FIG. 2 through 7, the surgical apparatus further has a sequencer 15 enabling formation of the pulsed jet and controlling its parameters.

According to a preferred variant, the conduit for passage of the pressurized liquid is, at certain times, depending on the characteristics of the pulsed jet, placed in communication with the aspiration system in order to improve the shape of the pressurized liquid pulse train and in accordance with an original feature also patented.

The active end 7 of the apparatus according to the invention may have a different form depending on the nature of the intervention to be performed. The end tube 8 may thus be relatively short in the case of interventions involving surface parts of the body or largely exposed tissues. The tube 8 may be longer when, for example, it must pass through a trocar to reach deeper tissues, with the intervention thus requiring only incisions of reduced size which are less traumatizing for the patient. According to another variant depicted in FIG. 4, the apparatus according to the invention is extended by a flexible tube 16, including the fluid circulation circuit(s) and capable of being introduced and guided within a catheter advanced to the operative site to perform non-invasive percutaneous interventions.

The active end 7 may also be articulated and adjustable in orientation and may include a reference system to enable its positioning at the appropriate location and at a preferred angle, with the unit controlled from the hand unit 4.

It may also include an anchoring system to provide for immobilization of the active end at the time of pressurized liquid blasts, thus improving the precision of the interventions. This may, for example, be any type of mechanical anchoring means, or a means utilizing the aspiration system of the instrument, such as the skirt 17 depicted in FIG. 4.

In order to permit the application of a treatment product, the dissection apparatus according to the invention further has a treatment product supply 18. According to the simplest embodiment of the invention, the treatment product constitutes the working liquid and is stored in the previously described supply 3.

The treatment product is preferably in liquid form or adequately fluid to be applied by means of the apparatus according to the invention. It may be a single therapeutic agent or a mixture of a plurality thereof, as a fluid or preferably as a liquid, for example, in solution or in suspension in any solvent or as an emulsion, a foam, or a gel, all under the necessary sterile conditions.

Since the cost of the treatment product is generally much higher than that of a working liquid, the apparatus according to the invention preferably has at least two separate supplies, the first 3 for the working liquid and the other 18 for the treatment product.

The treatment product supply 18 may also be a plastic pouch placed inside the same pressurization housing as the working liquid supply or in a separate but similar housing in order to be able to regulate the pressure of the treatment fluid independent of the working liquid.

Figure 1:
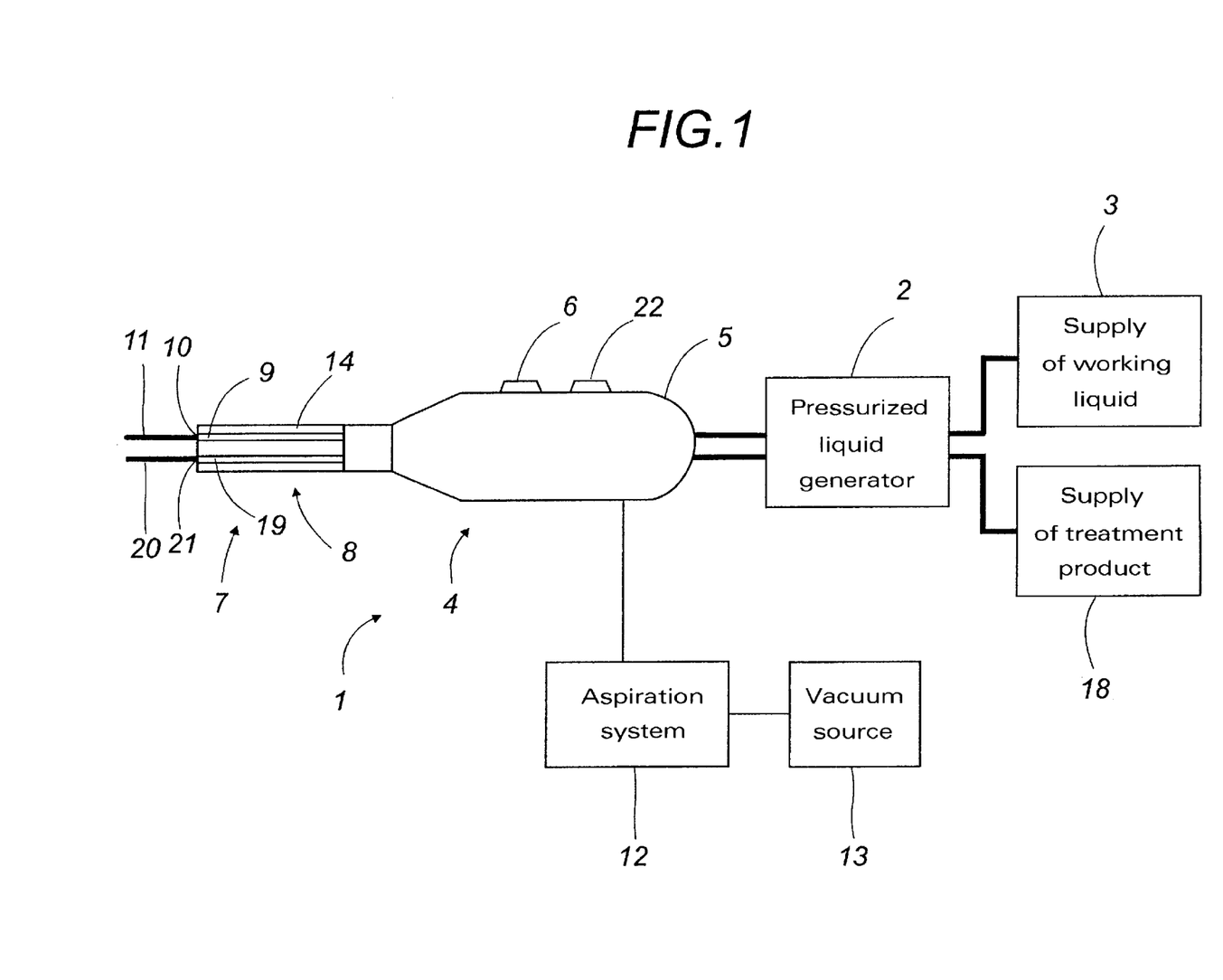
FIG. 1 is a simplified explanatory diagram of a pressurized continuous liquid jet dissection apparatus, including two independent circuits for the circulation and ejection of the working liquid and of the treatment product.
Figure 2:
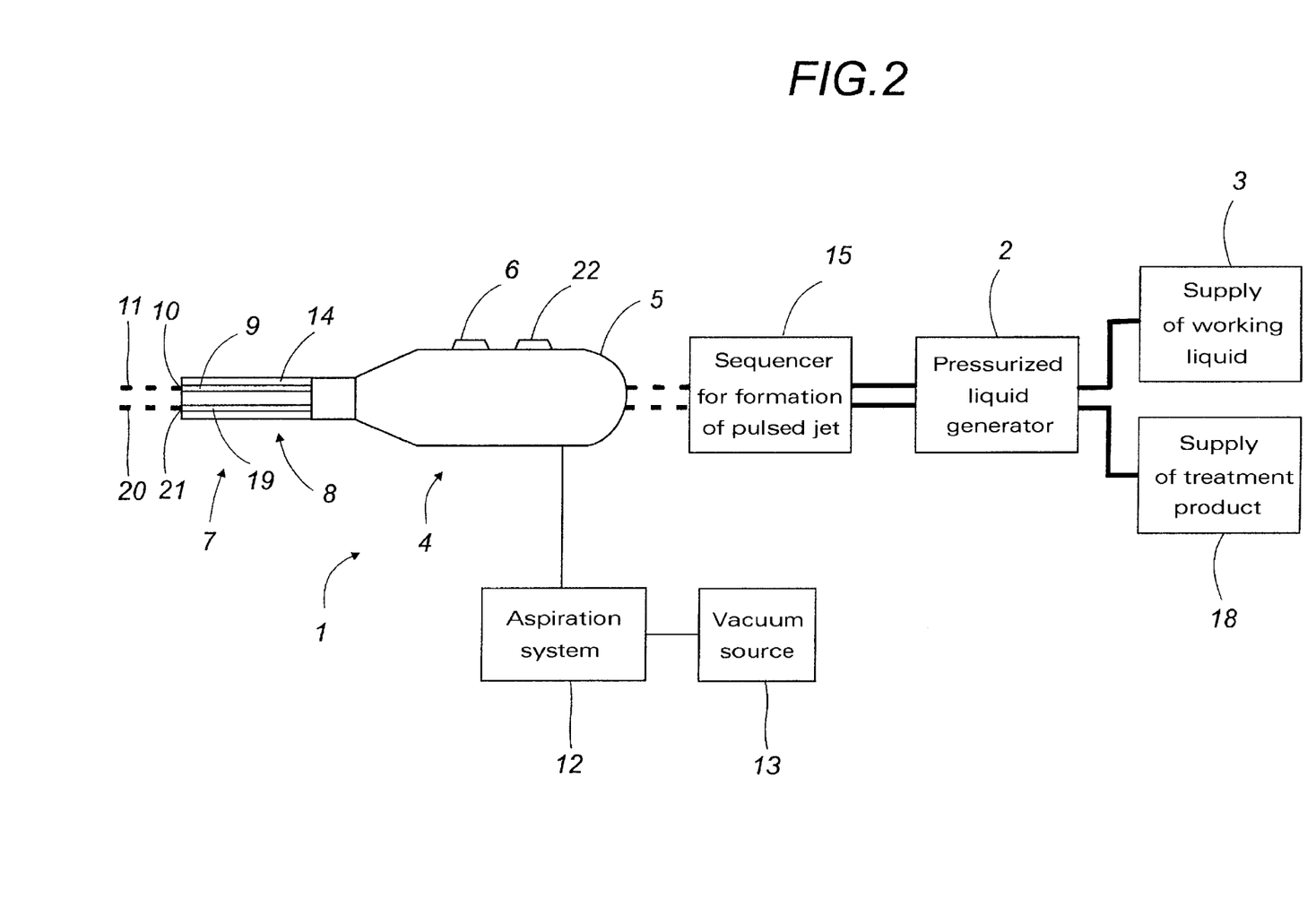
FIG. 2 is a simplified explanatory diagram of a pressurized pulsed liquid jet dissection apparatus, including two independent circuits for the circulation and ejection of the working liquid and of the treatment product.

As depicted in FIG. 1 and 2, the treatment product is then fed to the hand unit 4, through which it passes after traveling through a conduit 19 similar to the conduit 9 used by the working liquid, and discharges as a pressurized fluid jet 20 through an end orifice 21 similar to the end orifice 10. The triggering and stopping of the pressurized treatment fluid jet are controlled by the surgeon performing the intervention by means of a control element, such as a pushbutton 22.

The dissection apparatus according to the invention may also have only a single conduit 9 and a single end orifice 10 for both the working liquid and the treatment product, as depicted in FIG. 3 through 7.

Figure 5:
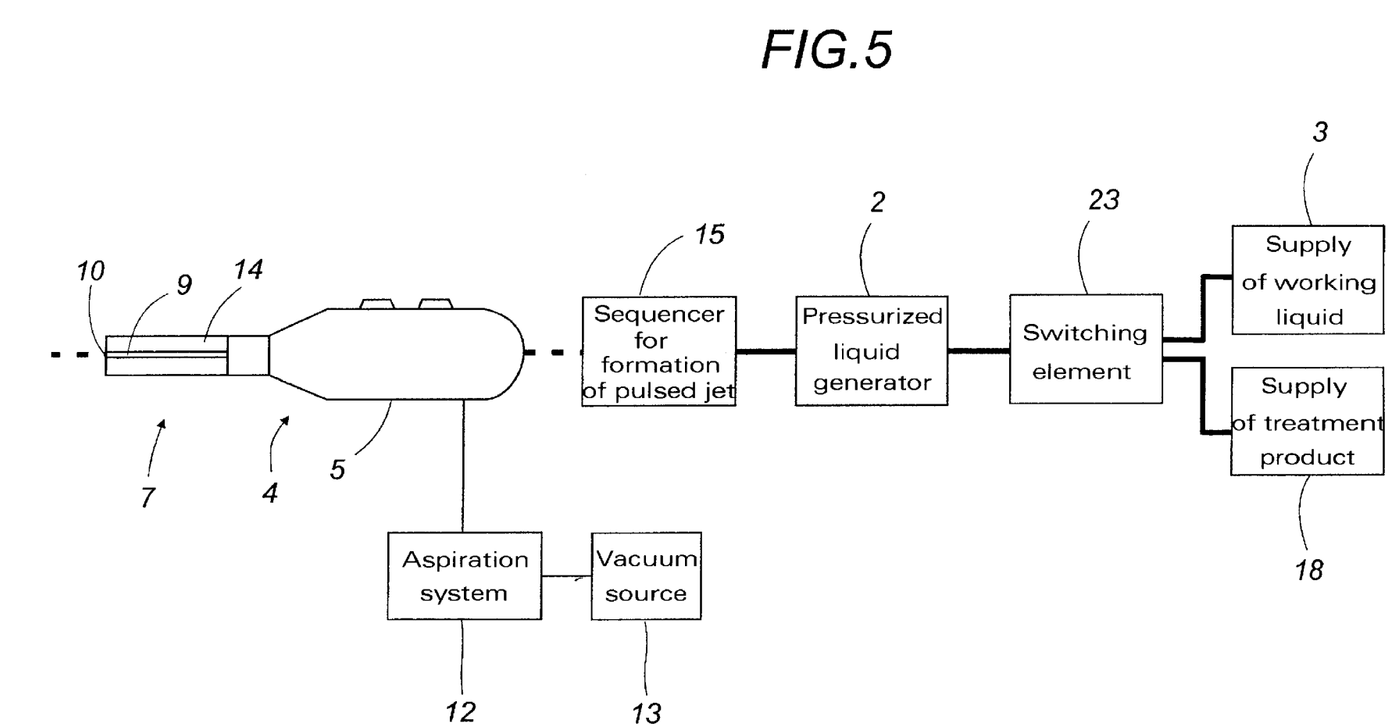
FIG. 5 is a simplified explanatory diagram of a pressurized pulsed liquid jet dissection apparatus, including a single circuit enabling alternating circulation and ejection of a working liquid or a treatment product, with the switching element placed before pressurization of the liquid.
Figure 6:
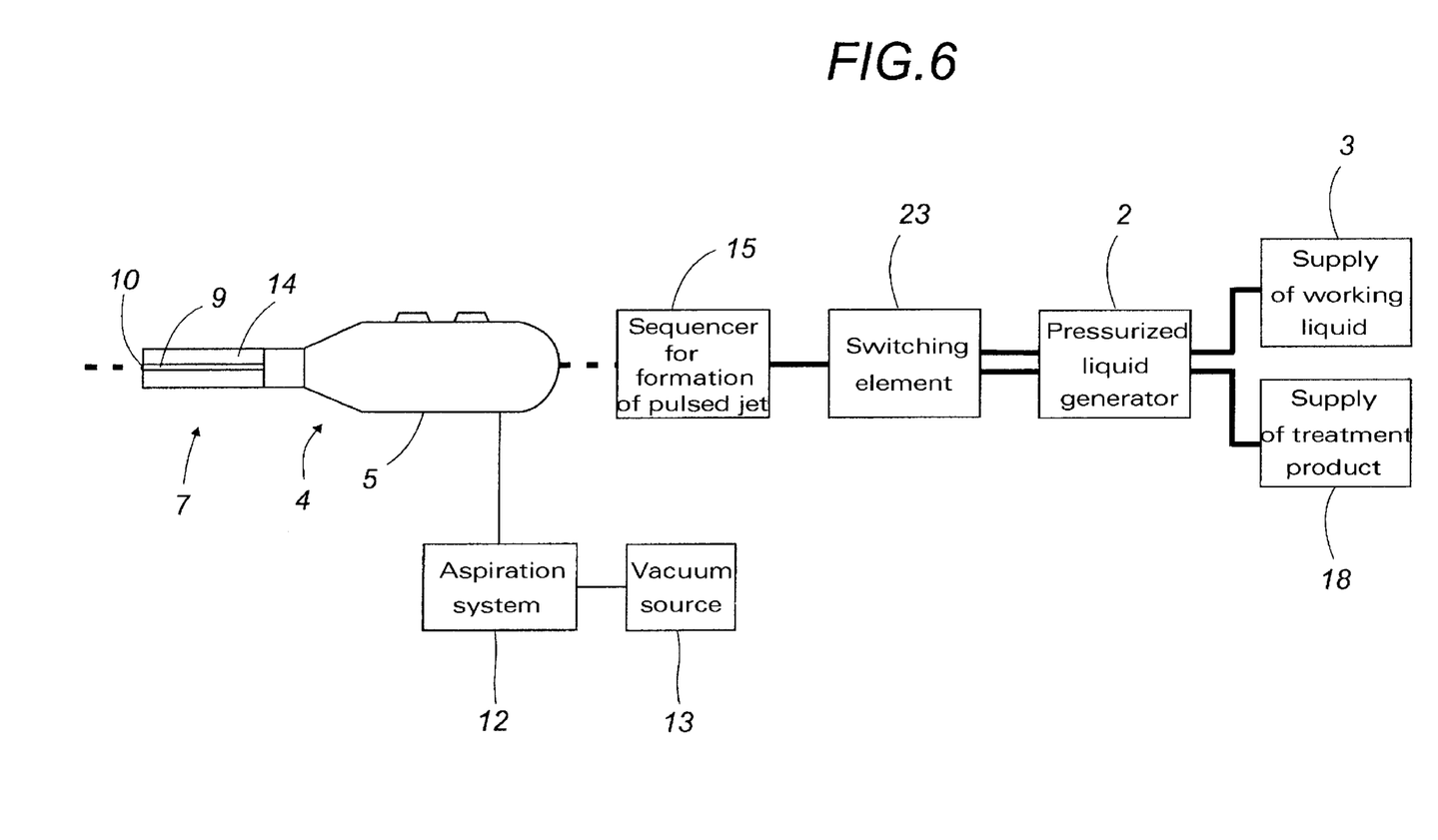
FIG. 6 is a simplified explanatory diagram of a pressurized pulsed liquid jet dissection apparatus, including a single circuit enabling alternating circulation and ejection of a working liquid or a treatment product, with the switching element placed after pressurization of the liquids.
Figure 7:
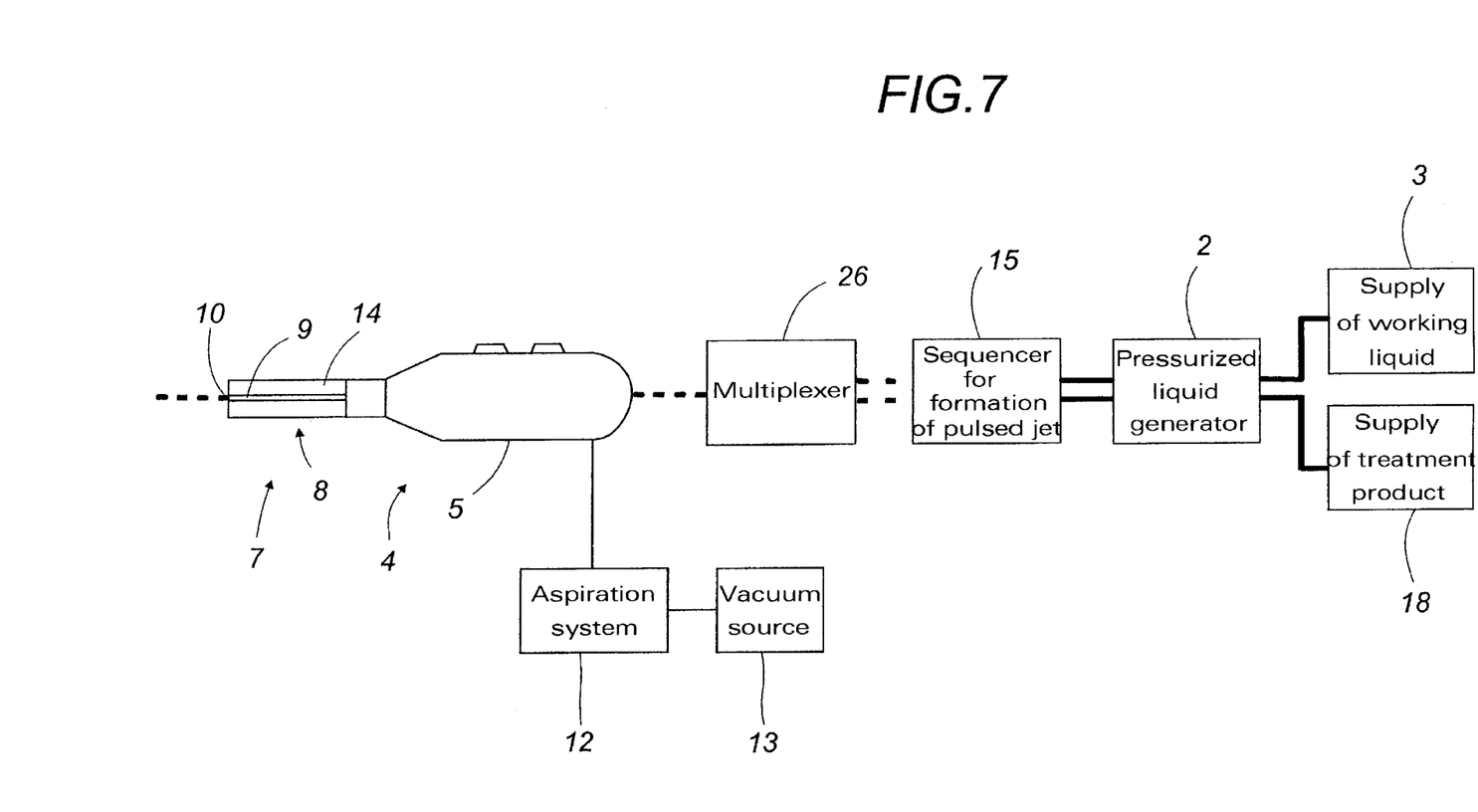
FIG. 7 is a simplified explanatory diagram of a dissection apparatus according to the invention enabling emission of a pressurized pulsed liquid jet made up of elementary pulses of working liquid and of a treatment product in a sequence, and based on parameters which can be modified and programmed according to need.

As depicted in the FIG. 5 and 6, the dissection apparatus may thus have, for example, upstream from this conduit 9, a switching element 23 enabling the surgeon performing the intervention to selectively start the blast from the orifice 10 of a working liquid jet or a treatment product jet. In FIG. 5 and 6, a blast of working liquid was depicted, represented by a heavy black line. However, thanks to the switching element 23, the surgeon may likewise elect to effect a blast of treatment product. This switching element can equally be located either upstream (FIG. 5) or downstream (FIG. 6) from the generator 2 enabling pressurization of the liquid(s).

The apparatus may also include, instead of the switching element 23, a mixing element 24 enabling the surgeon to mix working liquid and treatment product at the appropriate time. The mixing element 24 is controlled, manually or automatically, to realize a mixture of which the respective proportions of the different constituents were selected in advance. The mixing element 24 is placed upstream from the orifice 10 and the conduit 9 discharging there, at any level whatsoever of the apparatus according to the invention, being placed either before (FIG. 3) or after (FIG. 4) the pressurization of the liquid(s).

Figure 3:
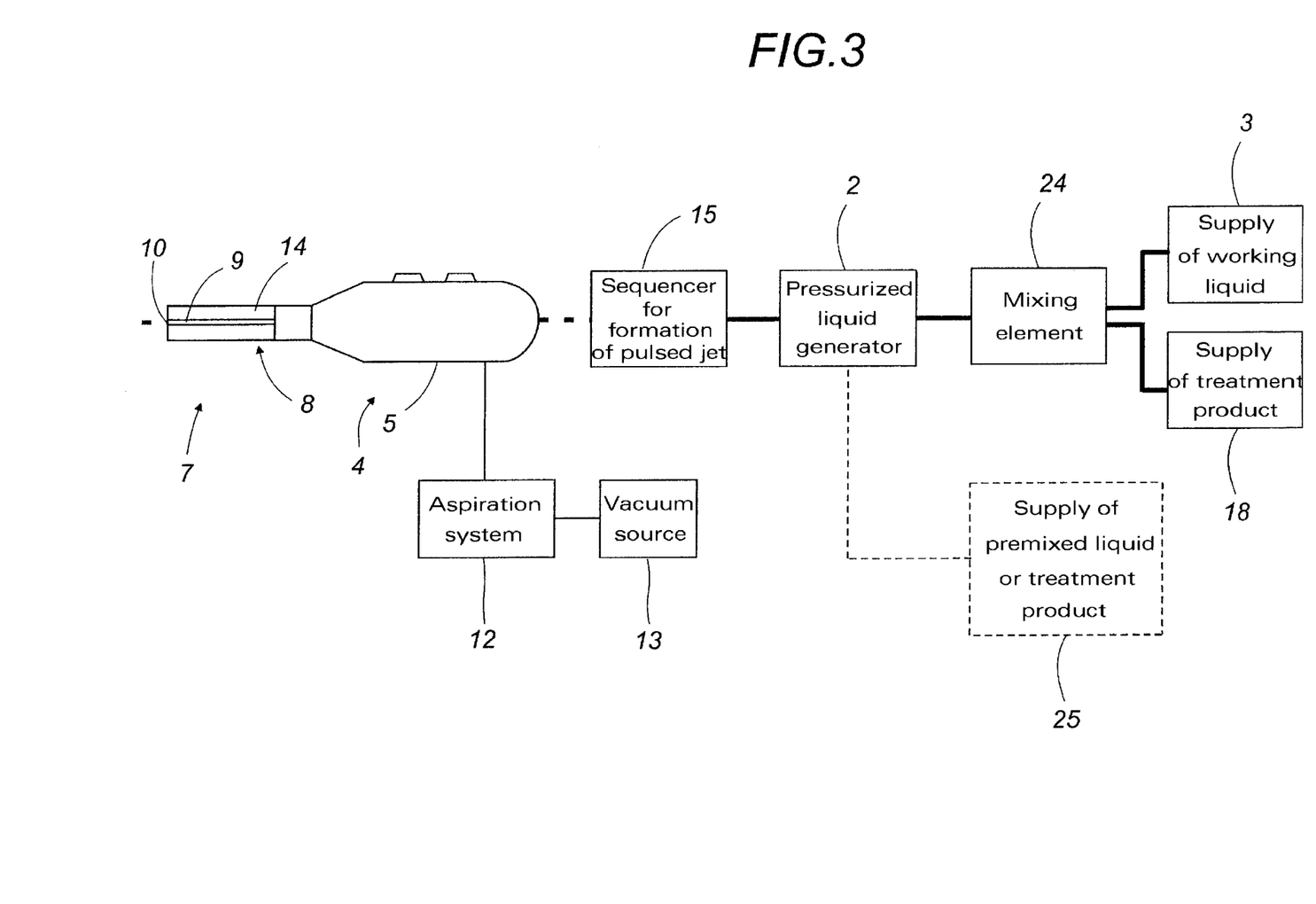
FIG. 3 is a simplified explanatory diagram of a pressurized pulsed liquid jet dissection apparatus, including a single circuit enabling the circulation and ejection of a mixture of working liquid and treatment product, with this mixture being effected before pressurization of the liquid.
Figure 4:
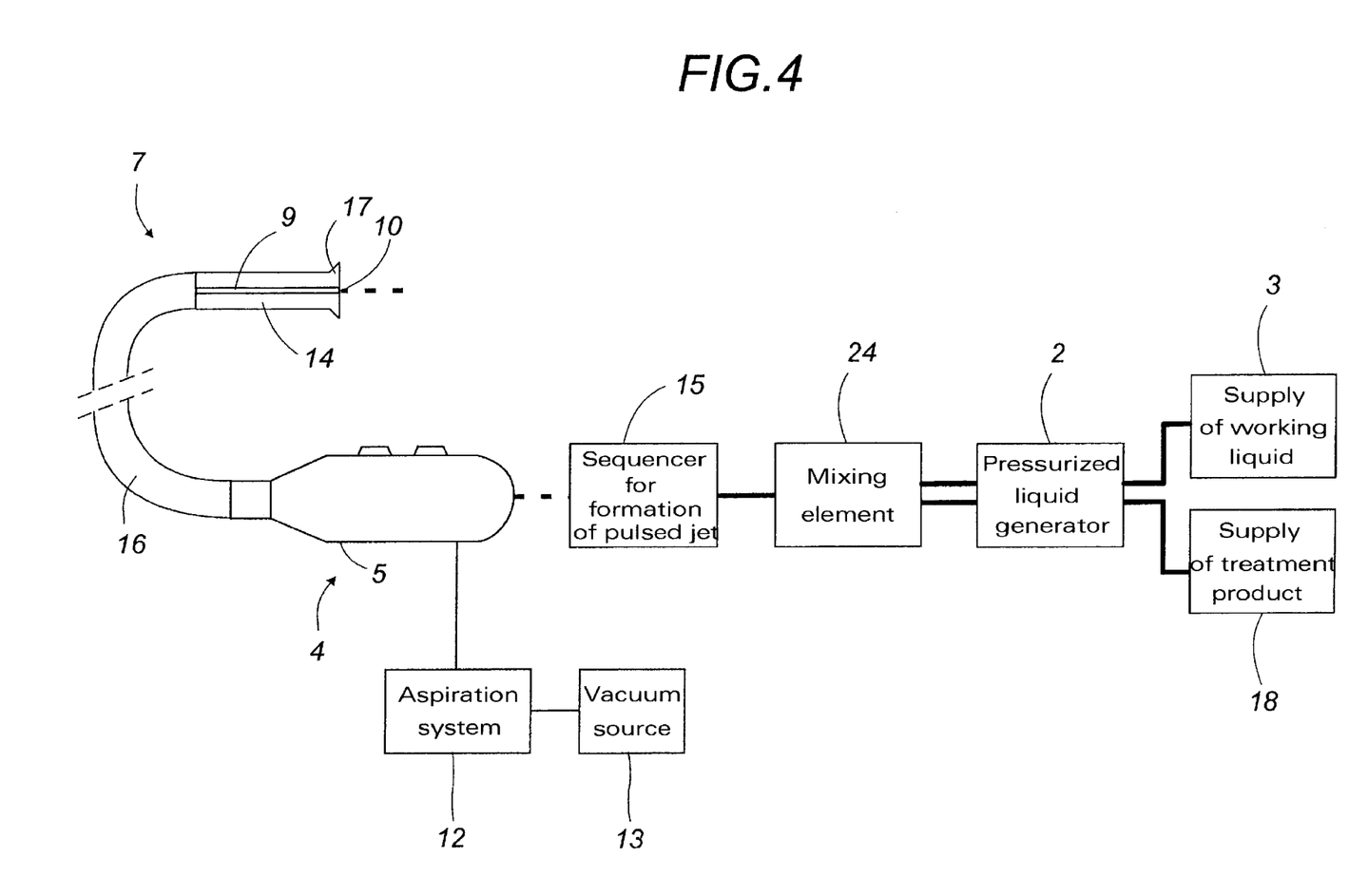
FIG. 4 is a simplified explanatory diagram of a pressurized pulsed liquid jet dissection apparatus extended by a catheter and including a single circuit enabling the circulation and ejection of a mixture of working liquid and treatment product, with this mixture being effected after pressurization of its components.

According to another variant depicted in light lines and dashed lines in FIG. 3, the working liquid supply 3 and the treatment product supply 18 may be replaced by a single supply 25 of pre-mixed liquid.

When, according to a preferred embodiment of the device according to the invention, the apparatus enables delivering a pulsed pressurized liquid jet, it may also include a multiplexer 26 enabling combining working liquid and treatment product pulses within the discontinuous pulse train making up the pulsed jet. The parameters of the various pulses, their nature, and their succession can be modified and programmed depending on the needs of the surgeon, of the patient, and of the type of intervention performed, in order to optimize the outcome of the intervention. This preferred embodiment of the apparatus according to the invention was depicted in FIG. 7.

Obviously, the invention is not limited to a procedure enabling the injection of only a single treatment product nor to an apparatus enabling injection of only a single treatment product. It is possible to conceive, in accordance with the invention, of a dissection procedure and an apparatus enabling application of various treatment products of different types, alternatingly, simultaneously, or mixed, by means of independent conduits and orifices, switching elements, mixing elements, a multiplexer alternating within a single pressurized pulsed liquid blast from elementary pulses of working liquid and/or of various treatment products, or of a combination of these different means. It is possible, for example, to conceive of a procedure according to the invention and an apparatus implementing it injecting first a preparatory agent for the surgery, then the working liquid in order to perform the dissection and simultaneously or immediately thereafter a second treatment product, this time having a therapeutic action.

The surgical apparatus according to the invention is, for example, particularly appropriate for performing interventions of the transmyocardial revascularization type, consisting in boring a plurality of revascularization channels into an ischemic zone of the myocardial wall.

The device according to the invention brings a significant improvement compared to the prior art revascularization apparatuses because it enables injecting a therapeutic liquid, directly at the level of the channels in the myocardium simultaneously with their creation. The application of the treatment liquid can also be carried out before or after the creation of the perforations. The treatment agent may be, for example, but not restrictively, an agent which prepares the muscle for the formation of the channels, promoting the development of new vessels, limiting clogging of the perforations, preventing postoperative complications, or any other agent useful in the event of surgical intervention or in the treatment of cardiovascular disorders.

Consequently, it is possible to combine the advantages of another treatment, for example, that of angiogenic therapy for the purpose of developing the vascularization of the ischemic zone of the myocardium with transmyocardial revascularization. During the course of this treatment, millions of copies of a gene promoting the creation of new vessels called vascular endothelial growth factor (VEGF) are injected directly into the ischemic region of the myocardium. This gene may also be injected indirectly by using a weakened virus as a transport vector.

With the device according to the present invention, a liquid containing the copies of this gene, the virus, or any other vector thereof may be applied at the time of creation of the perforations or immediately thereafter. This application may trigger, accelerate, or increase the angiogenesis which one is attempting to generate by the transmyocardial revascularization intervention.

Any other angiogenic substance may also be applied in the same manner. These may, for example, be other growth factors, such as fibroblast growth factors (FGF), and the mitogenic endothelial growth factors, or, for example, estrogens, such as estradiol, estriol, or 17 -β-estradiol.

Another example of application of the apparatus according to the invention and of the procedure implemented thereby is the treatment of vascular disorders such as thromboses.

The application to re-channel arteries obstructed by a thrombus will be performed using the apparatus according to the invention in its catheter version which may, for example, spray a high efficacy thrombolytic agent of the streptokinase or urokinase type by way of preparation. The task of fragmentation or disintegration of the thrombus can be carried out using the same pressurized liquid agent combining its biochemical action with that of the force of the pressure of the jet. A different, slow dissipation thrombolytic agent may be sprayed or diffused over the site after the evacuation of the thrombus by the aspiration system of the apparatus to neutralize the well-known tendency to form a new thrombus.

The apparatus according to the invention in its catheter version makes it possible to conceive of the cleaning and surfacing of the wall of the arteries with a view to recalibration of the vessels. The first phase consists of cleaning using the mechanical effect of the pressure and the effect of an agent promoting the dislodging of atheroma deposits and plaques. The exposed flesh will be smoothed and surfaced by the deposition of a finishing agent, for example, a surfacing agent.

The apparatus according to the invention, because of its adjustable intensity of dissection effect, is also particularly advantageous for interventions on soft tissue, such as that of the liver. It can be used advantageously to perform grafts, with a device according to the invention enabling simultaneous application of anti-rejection substances, or to remove cancerous tumors from this organ.

Surgery on a cancerous liver will enable ridding it of all its cancerous tumors through the combined action of a cytolytic agent and of the high pressure of the working liquid. It is possible to spray a preparatory agent on the site. Then, using the high pressure jet, the surgical task which consists essentially of cleansing the liver of its tumors is performed. The task of cutting and scraping using the mechanical effect of the high pressure jet shaped like a curtain enables efficient cleansing virtually free of hemorrhages due to the low incisive effect of the jet and the soft character of the tissues. All the arterioles are preserved.

The cytolytic agent sprayed locally aids in the disencrustation of the tumors and in their dissociation from the healthy tissues. Moreover, the spraying of a chemotherapy agent can prevent the taking of medications which fatigue the organism during the immediate postoperative phase.

Many other medical or surgical applications could be described without departing from the scope of the invention.

What is claimed is:

1. Procedure of surgical or medical intervention on the body of a living being using a surgical or medical apparatus of which the working fluid is a pressurized biocompatible liquid, characterized in that, during the course of the intervention and with this same apparatus, at least one treatment product, mixed or not with the working liquid, thus improving its penetration and diffusion into the tissues, is sprayed under pressure in order to realize in a single intervention and with the same apparatus a surgical act and a therapeutic act.

2. Procedure of surgical or medical intervention according to claim 1, characterized in that at least one of the treatment products is a liquid.

3. Procedure of surgical or medical intervention according to claim 1, characterized in that at least one of the treatment products is an emulsion.

4. Procedure of surgical or medical intervention according to claim 1, characterized in that at least one of the treatment products is a foam or a gel.

5. Procedure of surgical or medical intervention according to claim 1, characterized in that at least one of the treatment products is a preparatory agent for the surgical task.

6. Procedure of surgical or medical intervention according to claim 1, characterized in that at least one of the treatment products is a finishing agent of the surgical task or of surfacing.

7. Procedure of surgical or medical intervention according to claim 1, characterized in that at least one of the treatment products is a therapeutic agent useful in the treatment of the problem or the disease of the patient in question.

8. Apparatus for surgical or medical work using a pressurized liquid, having a working liquid reserve, pressurization means, and means of discharge of a pressurized jet, continuous or pulsed, of working liquid, characterized in that it also includes at least one treatment product supply connected to a hand unit which terminates in an active end having discharge means for a pressurized jet, continuous or pulsed, of at least one treatment product.

9. Apparatus for surgical or medical work according to claim 8, characterized in that a single supply serves simultaneously as the supply for the working liquid and for at least one of the treatment products.

10. Apparatus for surgical or medical work according to claim 8, characterized in that at least one of the pressurization means is a housing filled with a neutral gas at a pressure between 0.3 and 200 bar and heated to a temperature near or slightly higher than 37° C. in which is enclosed at least one plastic pouch serving as a supply for the working liquid or for at least one of the treatment products.

11. Apparatus for surgical or medical work according to claim 8, characterized in that the working pressure is between 0.3 and 100 bar.

12. Apparatus for surgical or medical work according to claim 11, characterized in that the working pressure is 30 bar.

13. Apparatus for surgical or medical work according to claim 8, characterized in that its active end includes a flexible tube which can be introduced and guided in a catheter advanced to the operative site.

14. Apparatus for surgical or medical work according to claim 8, characterized in that the means of discharge of at least one of the treatment products are the same as those of the jet of the working liquid.

15. Apparatus for surgical or medical work according to claim 8, characterized in that it further includes an element to mix the working liquid and at least one treatment product.

16. Apparatus for surgical or medical work according to claim 8, characterized in that it further includes a switching element enabling alternating the emission of a jet of working liquid or of at least one treatment product.

17. Apparatus for surgical or medical work according to claim 8, characterized in that it delivers a pressurized pulsed liquid jet and in that it further has a multiplexer enabling combining pulses of working liquid and at least one of the treatment products within a discontinuous pulsed train constituting the pulsed jet.

18. Apparatus for surgical or medical work according to claim 8, characterized in that it also has an aspiration system connected to a vacuum source.

19. Apparatus for surgical or medical work according to claim 8, characterized in that it also includes at least one control means enabling the person performing the intervention to trigger, to stop, and/or to modify the parameters of the jet of working liquid and of at least one treatment product.

* * * * *